United States Patent [19]

Montalbano et al.

[11] 3,995,768
[45] Dec. 7, 1976

[54] CARTRIDGE FOR APPARATUS FOR DESTROYING SYRINGES AND LIKE ARTICLES

[75] Inventors: Anthony P. Montalbano, Glencove, N.Y.; Erich Emil Hensel, Wassenaar, Netherlands

[73] Assignee: Madeline Ippolito, Great Neck, N.Y.

[22] Filed: May 23, 1975

[21] Appl. No.: 580,478

Related U.S. Application Data

[62] Division of Ser. No. 411,829, Nov. 1, 1973, Pat. No. 3,929,295.

[52] U.S. Cl. ............................................... 221/197
[51] Int. Cl.² ......................................... B65H 1/00
[58] Field of Search ............. 221/82, 83, 197, 287, 221/89, 90, 91, 106; 89/33 B

[56] References Cited
UNITED STATES PATENTS 1,286,810  12/1918  Sheppard .................... 221/91 UX
3,656,655  4/1972  Magnoville ........................ 221/82

*Primary Examiner*—Allen N. Knowles
*Attorney, Agent, or Firm*—Flynn & Frishauf

[57] ABSTRACT

Apparatus for destroying medical syringes, or the like articles, comprises a plurality of spaced stationary members having serrations over a portion of a given surface thereof and a plurality of rotatable members, preferably round and preferably serrated around the whole periphery thereof, mounted between adjacent stationary members, an entrance path being formed between the rotatable and stationary members. The entrance path tapers from an entrance dimension larger than the maximum lateral dimension of the syringe to a dimension at least substantially smaller than the maximum dimension. Further provided is a cartridge arrangement for the apparatus and a unique feeding arrangement to insure that the syringes, or the like articles, properly enter the entrance path.

10 Claims, 14 Drawing Figures

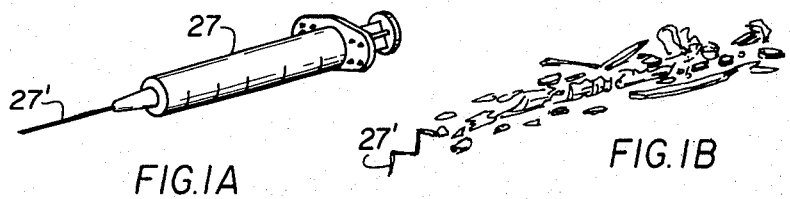
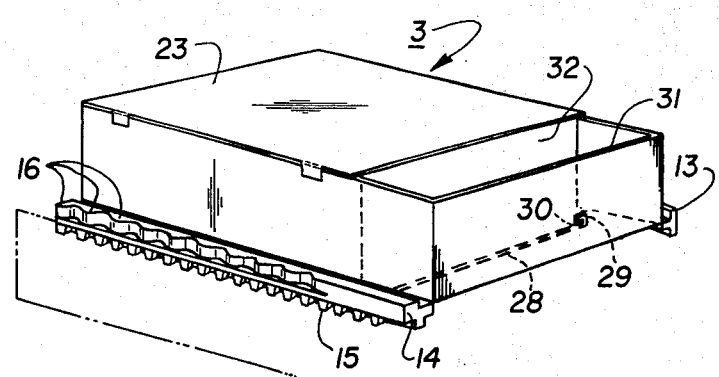
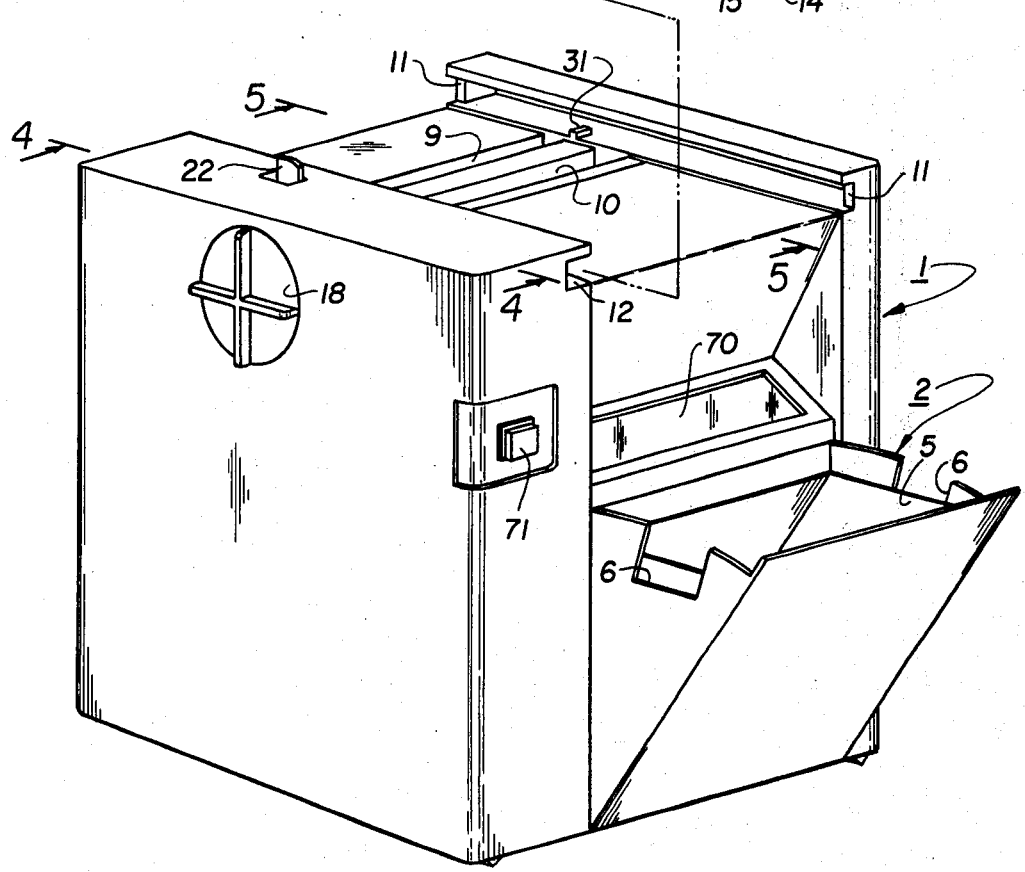

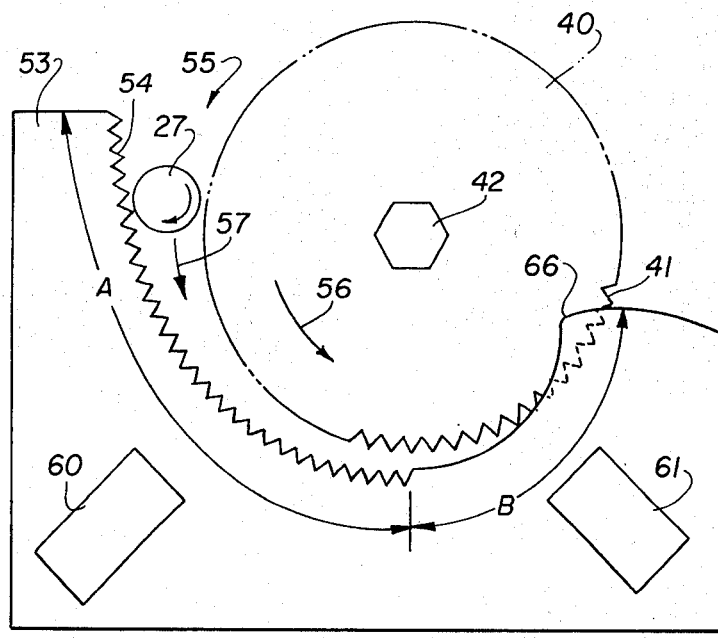
FIG. 7
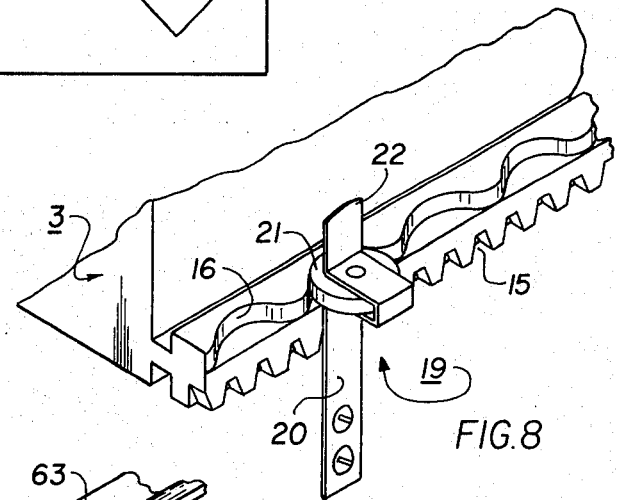
FIG. 8
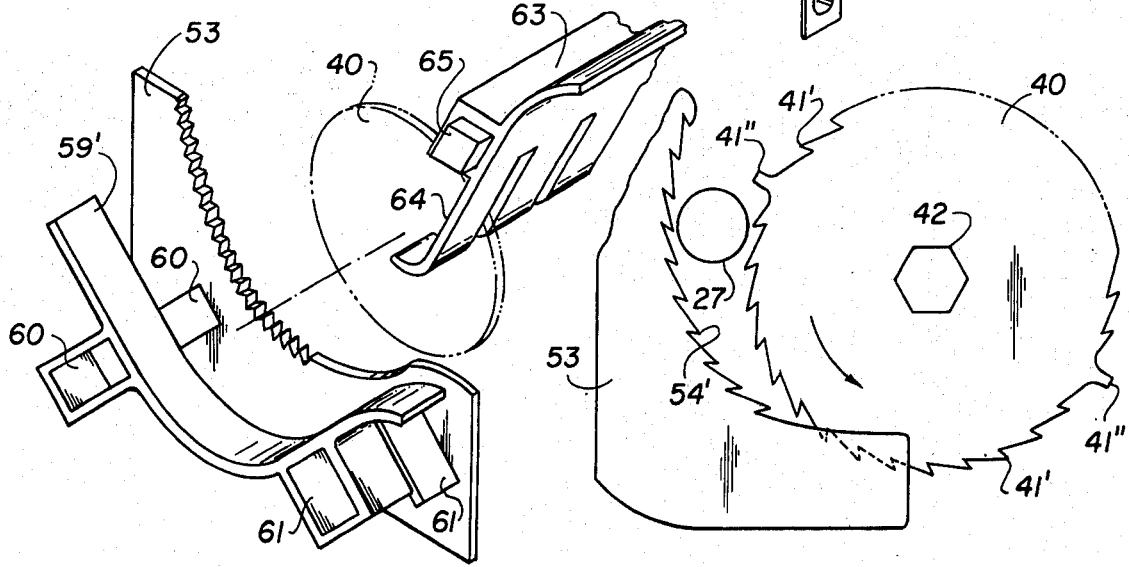
FIG. 9
FIG. 13

CARTRIDGE FOR APPARATUS FOR DESTROYING SYRINGES AND LIKE ARTICLES

This is a Division of application Ser. No. 411,829, filed Nov. 1, 1973, now U.S. Pat. No. 3,929,295, issued Dec. 30, 1975.

This invention relates to destruction devices, and more particularly to destruction devices for destroying medical syringes, or the like articles.

Prior art destruction devices for medical syringes are known. However, such prior art devices generally operate at relatively low speed and are capable of handling small quantities of syringes for destruction per unit time. Further, in some known devices it is necessary for the operator of the destruction device to physically handle each syringe to be destroyed and to individually insert each syringe into the destruction device, thereby rendering operation of the destruction device a hazardous matter. Inadvertent pricking of the skin by a syringe which is to be destroyed could, in some cases cause serious illness, such as hepatitis.

The main object of the present invention is to provide a destruction device capable of efficiently destroying medical syringes or the like, at a high speed, and which does not require the individual handling of each syringe (after patient admistration) to be destroyed.

A further object of the present invention is to provide such a destruction device which may be operated with cartridges so as to completely eliminate the necessity for the operator to handle the individual syringes after application.

A further object of the present invention is to provide such a destruction device which is capable of handling a plurality of different sizes of syringes with substantially equal destruction efficiency.

A still further object of the invention is to provide a small, compact destruction unit which is capable of quickly and efficiently destroying syringes on an individual basis, thereby rendering the device useful in small, low volume installations. A further object of this aspect of the invention is to provide such a small, compact unit which provides maximum safety to the user so as to prevent inadvertent pricking of the skin by the syringe under destruction.

SUMMARY OF THE INVENTION

According to the present invention, apparatus for destroying medical syringes, or like articles includes at least one rotatable member having serrations along at least a portion of the periphery thereof, and at least one stationary member having serrations over at least a portion of a given surface thereof which faces the periphery of the rotatable member. The rotatable member is mounted laterally offset relative to the stationary member, and a given surface of the stationary member which faces the periphery of the rotatable member has a shape which defines an entrance path between the at least one rotatable member and the at least one stationary member, the entrance path tapering from a entrance dimension larger than the maximum lateral dimension of the syringe to a dimension at least substantially smaller than the maximum lateral dimension of the syringe. Preferably, the apparatus includes a plurality of rotatable members, which are perferably disk-shaped, and a plurality of spaced stationary members, the rotatable members being interposed between the spaced stationary members. The serrations on the rotatable and stationary members are such as to promote positive feeding of the syringe, or the like article, through the entrance path so as to be destroyed effectively.

According to another feature of the invention, means are provided for feeding the syringe, or the like article in a substantially horizontal orientation into the entrance path between the stationary and rotatable members. The feeding means preferably defines a tortuous path with at least two changes of directions of the syringe, and the means forming the tortuous path preferably includes a plurality of flat, plate-like sections.

According to a further feature of the invention, a novel cartridge arrangement is provided for feeding syringes into the destruction device, a plurality of cartridges being provided so as to enable simplified and safe collection of syringes at a plurality of locations for ultimate destruction by the apparatus. Each cartridge preferably has a plurality of chambers therein, each chamber accommodating a plurality of syringes. In accordance with a preferred type of cartridge, the cartridge has a slideable bottom which engages the housing of the apparatus so that successive chambers feed syringes into the entrance upon advancing of the cartridge relative to the housing.

According to another feature of the invention, a destruction device includes a feed mechanism which is interlocked with a slideable controller for simultaneously feeding a syringe into the entrance path between the rotatable and stationary members, and closing the feed opening of the device so as to prevent dropping of further objects into the apparatus during operation. Preferably, the slideable controller is interlocked with the on-off switch to automatically turn the device on when the controller is operated.

Various other features and objects of the invention will become more apparent from the following detailed description of preferred embodiments of the invention when taken in conjunction with the accompanying drawings.

BRIEF DESCRIPTION OF THE DRAWINGS

FIG. 1A generally illustrates a typical medical syringe which is to be destroyed;

FIG. 1B illustrates how such a typical syringe would appear after passing through the destruction device of the present invention;

FIG. 2 is a perspective view of a cartridge-type apparatus according to the present invention;

FIG. 7 is an enlarged view of the destruction apparatus with a syringe in the process of being destroyed;

FIG. 8 shows the detent-type engagement arrangement for positively engaging the cartridge with the housing of the apparatus of the present invention;

FIG. 9 is a perspective view of a portion of the destruction device showing some of the elements thereof in more detail;

FIG. 12 is a partial sectional view, similar to FIG. 11, showing the insertion mechanism in the fully operational state which automatically turns the device on; and FIG. 13 shows a modified form of the destruction mechanism.

DETAILED DESCRIPTION OF ILLUSTRATED EMBODIMENTS

Referring to FIG. 1, there is generally illustrated a medical syringe of the type which is to be destroyed by the apparatus according to the present invention. FIG. 1A illustrates the syringe before insertion into the device, and FIG. 1B illustrates a typical syringe after passing through the destruction device. In many instances, however, the syringe will be destroyed to a greater degree than illustrated in FIG. 1B, and will be in a plurality of individual separated pieces. The illustration in FIG. 1B is merely given by way of example to illustrate that the syringe is completely unusable after being passed through the device of the present invention. The syringes presently being used are of a plastic composition, but it should be clear that the device according to the present invention is suitable for use with any type of syringe. Moreover, while the present application is directed to use of the destruction device with medical syringes, it should be clear that the destruction device of the present invention could be used for many other purposes to destroy, crush or otherwise break up other types of articles, especially elongated articles. The present application and the appended claims, are to be construed to include such use of the present invention.

Figure 5:
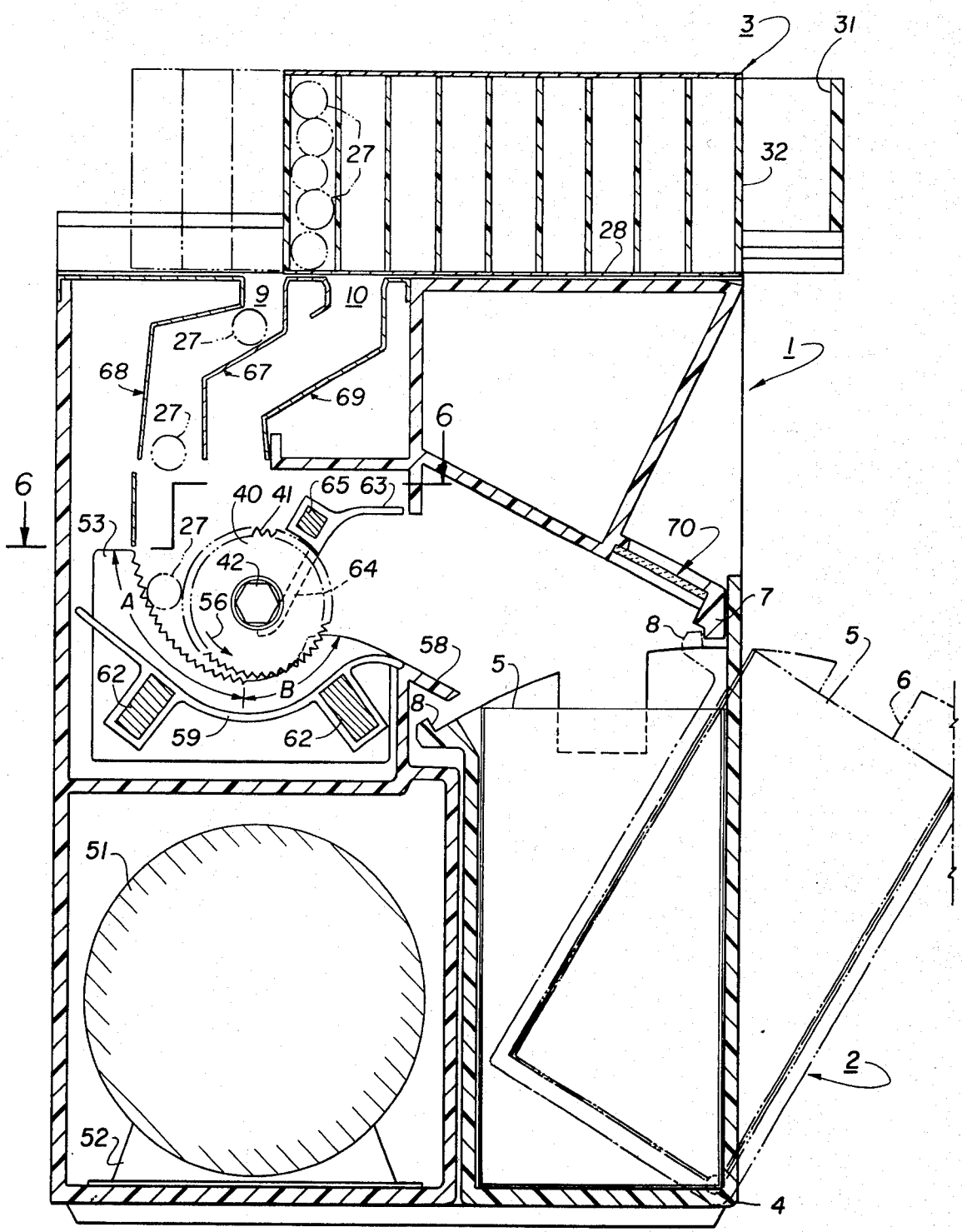
FIG. 5 is a sectional view taken along the line 5—5 in FIG. 2 showing the destruction apparatus in greater detail.

Referring to FIG. 2, the device of the present invention includes a housing 1 with an openable chamber 2 for receiving destroyed syringes. Removably fitted to the top of the housing 1 is a cartridge 3, the internal construction of which is illustrated in more detail in FIG. 5 and which will be discussed in more detail hereinbelow. The chamber 2 is pivotably connected to the housing 1 by means of pivot 4 (FIG. 5) and contains a removable and disposable liner 5 which may be a plastic or paper bag, or a cardboard type of box which is slideably inserted into the chamber 2 for receiving the destroyed syringes. The chamber 2 has side cut-out portions 6 to facilitate removal of the liner 5. As shown in FIG. 5, the housing has a stop member 7 inside thereof and the chamber 2 includes a corresponding stop member 8 which engages the stop member 7 to limit the outward movement of the chamber during removal of the liner 5.

The housing 1 has an upper surface having two syringe insertion slots 9 and 10 (see also FIG. 5). Slot 9 has a smaller width than slot 10 (as clearly shown in FIG. 5), the two slots being designed to receive different size syringes. It should be clear that a greater number of slots 9, 10 could be provided, as desired, or one slot could be provided for accepting all sizes of syringes, depending upon the particular requirements of individual systems.

Figure 4:
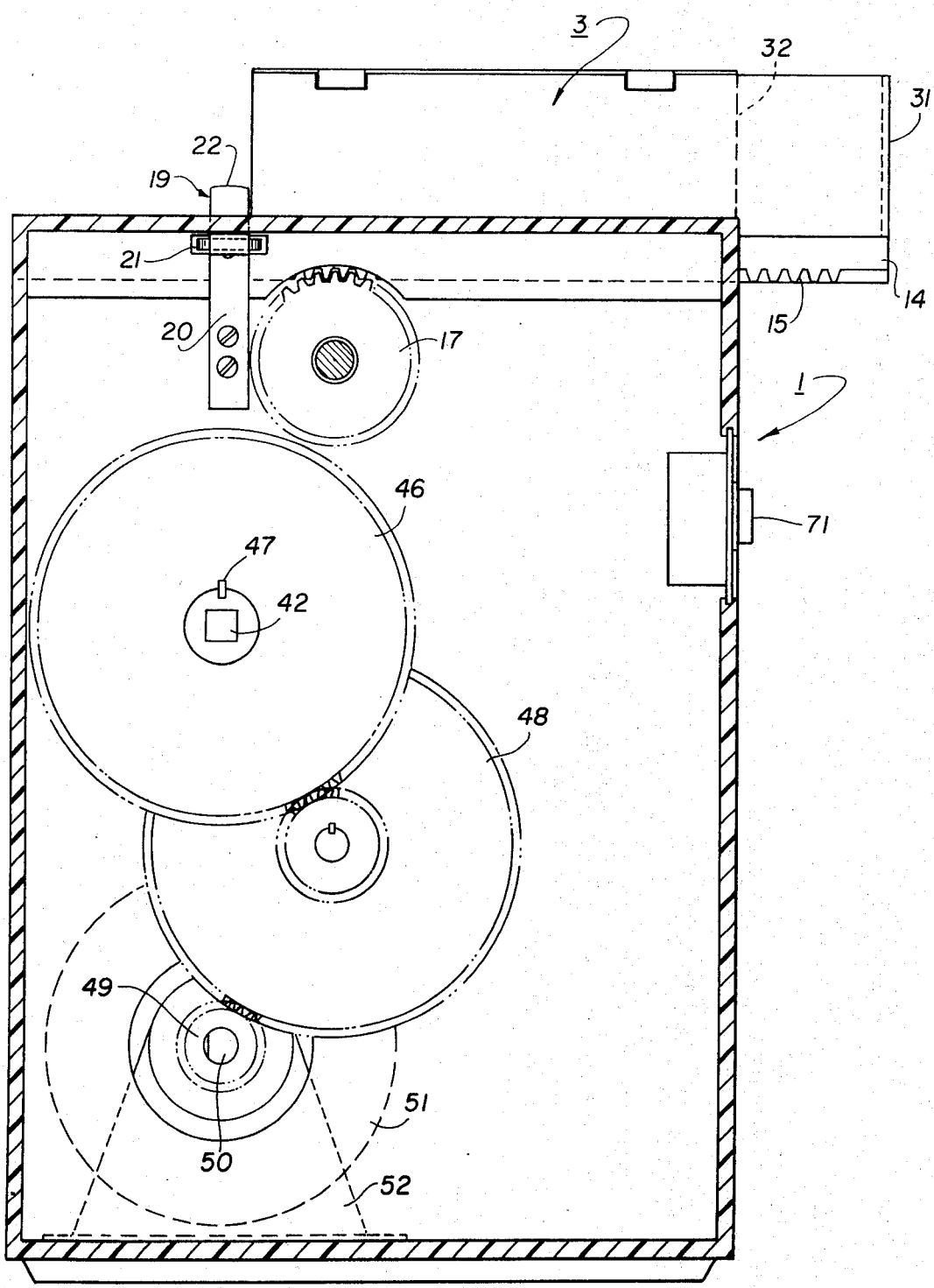
FIG. 4 is a sectional view taken along the line 4—4 of FIG. 2 showing a portion of the internal operating mechanism.

The housing 1 further includes elongated slots 11 and 12 which respectively receive elongated protruding rail-guide members 13 and 14 cartridge 3. Rail-guide member 14 of cartridge 3 has a rack-type gear 15 on the lower surface thereof and a plurality of detents 16 on a side surface thereof. As shown in FIG. 4, the rack 15 engages a gear 17 which is operatively coupled to an operating knob 18 (FIG. 2) for advancing the cartridge member 3 relative to the casing 1 of the destruction device. The indentations 16 engage a detent mechanism 19, shown in detail in FIGS. 4 and 8. Detent mechanism 19 is comprised of, for example, a spring-metal member 20 secured at its lower end to the housing 1 or other fixed member of the device, and a wheel member 21 rotatably connected to the spring member 20. The spring member 20 biases the rotating wheel 21 in the direction of the indentations 16 so as to positively engage the cartridge at fixed positions along the length of the slot 12. The spring-metal member 20 has an upper portion 22 which extends above the upper surface of the housing 1 for use in releasing the detent mechanism from the indentations 16 of rail 14. In order to quickly remove the cartridge from the housing 1, the member 22 is pulled toward the left in FIG. 2 so as to release the wheel 21 from the indentations 16, thereby facilitating removal of the cartridge 3 from the device.

Figure 3:
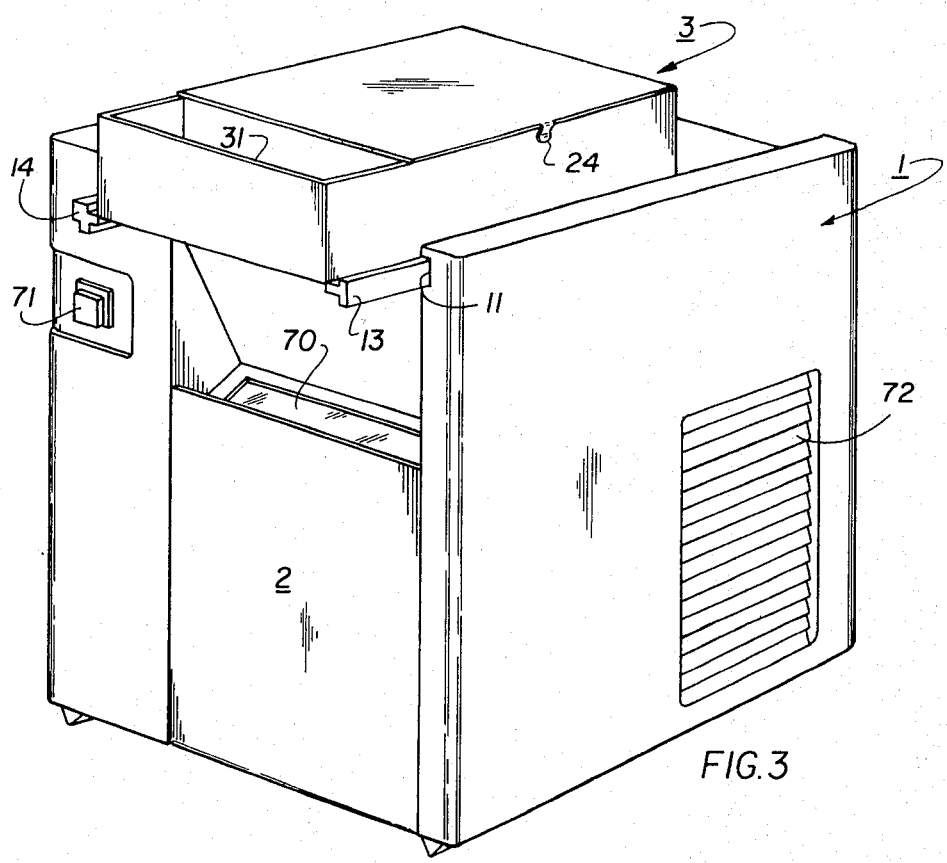
FIG. 3 is a perspective view from a different angle of the apparatus of FIG. 1 showing the cartridge in place and showing the waste disposal door in the closed position.

The cartridge 3 has an upper cover 23 which may be hingedly connected to the base portion of the cartridge, or which may be removably connected to the base portion. The cover 23 is retained on top of the cartridge 3 by means of a clasp member 24, which may be any type of well known device. The cartridge 3 also has an end handle portion 31 as seen in FIGS. 2, 3 and 5 to facilitate handling thereof, especially during insertion in and removal from the main housing 1. The operator's hand is received in the void space formed between member 31 and the adjacent end wall 32 of the syringe retaining portion of the cartridge 1. Preferably, the cartridge is fabricated of plastic, or the like, and is preferably autoclavable. As shown in FIG. 5, the cartridge 3 has a plurality of vertical partitions 25 dividing the internal portion of the cartridge into a plurality of vertical chambers 26. The cartridge may be pre-loaded with a plurality of syringes 27 stacked, for example, as shown in FIG. 5. The cartridge 3 further includes a base member 28 which is slideably engaged to the cartridge housing so that successive internal chambers 26 of the cartridge 3 are exposed to, for example, syringe insertion slot 9, during advancement of the cartridge 3 relative to the housing 1. The base 28 is secured to the cartridge 3 housing, for example, by means of lips 29 which slideably engage the corresponding protruding portions 30. The base member, and its mechanism enabling sliding thereof relative to the cartridge 3 in use will be discussed hereinbelow.

A stop member 31 is provided on the upper portion of the housing 1 (FIG. 2) for engaging the base 28 of cartridge 3. When the cartridge 3 is inserted into the housing 1, advancement of the cartridge body 3 is accomplished by rotating knob 18, or by pushing the cartridge 3 manually, and the base 28 is retained in a fixed position by means of the stop 31, thereby successively exposing the internal chambers 26 of the cartridge to the slot 9 in the housing of the device. This successively feeds the contents of the chambers 26 to the destroyer mechanism. The stop 31 is low enough so as to allow the cartridge housing 3 to pass thereover.

Referring particularly to FIGS. 5, 6, 7 and 9, the actual mechanism for destroying a syringe will be discussed in more detail. The destruction mechanism comprises a plurality of toothed wheels 40, having "teeth" or "serrations" 41, along the outer circumference thereof. The toothed wheels 40 are mounted to a rotatable shaft 42, one end of which is rotatably journalled in the end wall 43 of a frame 44. The other end of rotatable shaft 42 passes through the other end wall 45 of the frame 44 and is connected to a gear 46 which drives the shaft 42 via a key-locking arrangement 47. Gear 46 is driven via a gear 48, which in turn is driven via a gear 49 which is connected to the shaft 50 of a motor 51. The motor 51, is mounted to the base of the housing 1 by means, for example, of mounting brackets 52 and the gear 48 is rotatably coupled to the housing 1. The teeth 41 may be as shown in FIG. 1, or may be "angled" teeth 41', for example as shown in FIG. 13, to provide, in some cases, a better "bite" into the article being destroyed. Teeth 41 may take various shapes, depending upon use of the device. Also projections 41'' as shown in FIG. 13 may be provided as desired, to urge the articles to be destroyed downward.

Fixedly mounted to the frame 44 are a plurality of fixed cutter members 52 which have teeth or serrations 54 along a substantial portion of the curved surface thereof, as illustrated, for example, in FIGS. 5 and 7. The teeth 54 may be angled teeth 54' as shown in FIG. 13 or may take any other convenient shape, depending upon use. The curvature of the toothed portion of fixed cutter 53 is correlated to the rotatable toothed wheels 42 such that at the entrance portion 55, sufficient clearance is provided so as to receive a syringe, such as syringe 27 of FIG. 7. As the rotatable toothed wheels 40 rotate in the direction of the arrow 56 (FIG. 7), the syringe 27 is engaged by the teeth or serrations 54 and 41 and is quickly and positively drawn downward in the direction of the arrow 57 (FIG. 7) whereby it is crushed and/or mutilated by engagement between the fixed cutter members 53 and rotatable toothed wheels 40. Upon continued rotation of the wheels 40, the destroyed syringe 27 is ejected, passing over the guide member 58 and into the liner or receptacle 5 of the refuse chamber 2. A base portion 59 is provided below the wheels 40 to catch and retain any debris which drops during the cutting operation. It has been found that any debris which is collected on base member 59 is positively ejected from the system during the cutting and destruction of the next successive syringes by virtue of the engagement of the debris with downward protruding portions of the syringe during the destruction process. The debris is thus engaged and likewise brought out to guide member 58 for deposit into the refuse chamber 2. In the present embodiment, the base portion 59 comprises a plurality of segments 59' (FIG. 9) interposed between adjacent fixed cutting members 53. The fixed cutting members 53 have apertures 60 formed therein, and the base portion segments 59' have apertures 61 formed therein. Bar members 62 (FIG. 5) are passed through the apertures 60 and 61 so as to maintain the individual elements in the appropriate assembled state. Bar members 62 are anchored in the ends of frame 44 so as to maintain the elements with the proper structural integrity.

Further provided is a deflector member 63 having extending finger portions 64 which respectively extend between adjacent toothed wheels 40. The deflector 63 is anchored to the frame 44 by means of, for example, protrusions 65 which engage indentations in the end member 43 and 45 of the frame. The protruding ends 65 may be alternatively replaced with a bar or rod member extending through a corresponding aperture in the deflector member 63, the ends of the bar or rod member being anchored in the frame 44. Such an alternative construction would provide reinforcement to the deflector 63.

While the destruction device comprising fixed cutters 53 and toothed wheels 40 will satisfactorily destroy syringes if they are toothed along the complete length thereof, repeated experiments have shown that improved destruction capabilities are achieved if the wheels 40 are toothed around the complete circumference thereof, and if the fixed cutters 53 are toothed or serrated to an extent such that at a point about where there is no longer any lateral clearance between the wheels 40 and fixed cutters 53, the teeth or serrations 54 are ended. In this connection, reference is made to FIGS. 5 and 7, wherein such an advantageous toothed structure is illustrated. The section A of the fixed cutters 53 are serrated, whereas the section B is smooth. Further, the end portion of the section B is upwardly curved so as to protrude into the interstices between adjacent wheels 40. This construction is clearly illustrated in FIG. 7 and has been found to be particularly advantageous in promoting quick and efficient destruction of syringes or the like.

The upwardly curved cutter portion 66 has been found to be particularly effective in destroying the needle portion 27' (FIG. 1) of the syringe. In particular, reference is made to FIG. 1B wherein the metal needle portion 27' is bent beyond use.

Referring to FIG. 5, it is clearly seen that the syringes 27 are fed into the cutting and destruction arrangement via a tortuous path. This is to insure that the syringes 27 are received between the cutters and the rotating wheels of the destruction device in a direction substantially lateral of the device (that is, in a horizontal direction or in a direction substantially parallel with the axial direction of the shaft 42). As shown in FIG. 5, a typical needle 27 drops through slot 9, impacts and rolls down a conveying portion or partition wall 67, is then caused to impact the substantially vertical portion of the partition wall 68 and then falls in a substantially lateral or horizontal condition into the destruction mechanism, as shown. By virtue of this specially arranged tortuous path defined by the partition walls 67 and 68, proper feeding of the syringe, and proper landing of the syringe in the destruction mechanism is insured. A similar tortuous path, defined by specially shaped partitions 67 and 69, is provided for input slot 10, also as shown in FIG. 5. The three partitions 67, 68 and 69 are specially designed to make horizontal any syringes which deviate from the horizontal when fed into feed slots 9,10. It is also pointed out that the cartridge 3 with its partitions 25 also serves as a positive means of forcing the operator of the device to properly orient the syringes for proper reception by the destruction mechanism.

It has been found that at least two changes of direction in passing through the tortuous path defined by the bent partitions 67, 68 and 69 between the slots 9,10 and the destruction mechanism, per se, is required to provide best feed results for syringes generally encountered in the medical field. If desired, more changes of directions can be provided merely by varying the shapes of walls 67, 68 and 69 and by adding additional appropriately shaped conveying walls, if necessary.

A further advantage to the provision of the tortuous path feed of syringes is to insure that the syringes feed one-at-a-time into the cutters of the cutting mechanism. By changing the direction of the movement of the syringes by means of the walls or partions 67, 68 and 69, bunching up of the syringes in the cutting mechanism is effectively prevented.

Preferably, the cutting mechanism which is mounted to frame 44 is completely removable from the apparatus and is autoclavable for sanitary purposes. In this regard, it should be clear that the frame 44 carries the rotatable wheels 40, the fixed cutters 53, the base 59 and deflector 63, and comprises a complete integral unit which is connectable to the drive mechanism via gears. If desired, depending upon the application, a direct drive arrangement could be provided for the rotatable wheels 40.

Experiments have shown that for use in destroying syringes of the type generally used, which are made of plastic material and have metal needle portions, best destruction results are obtained when the rotating wheels 40 rotate at relatively high speeds, such as at about 230 rpm. With the plastic syringe bodies presently being used, slow speed operation of the wheels does not provide an effective shattering effect to the plastic. The high speed of rotation produces high impacts to the needle body and aids in shocking the plastic into fragments to provide more effective destruction of the syringe. However, the speed of rotation of the wheels 40 may be varied, depending upon the item being destroyed, to provide the desired destruction results.

Referring to FIGS. 2 and 3, the apparatus of the present invention is further provided with a window 70 through which the operator of the device may observe the contents of the disposal chamber 2. When the disposal chamber 2 is observed to be full or nearly full the operator can merely open the chamber and remove the liner 5. An on-off switch 71 is operatively coupled to the motor 51 by means not shown so as to turn the apparatus on and off. Air vents 72 are provided adjacent the motor 51 for cooling of the motor. See FIGS. 2 and 3.

Figure 6:
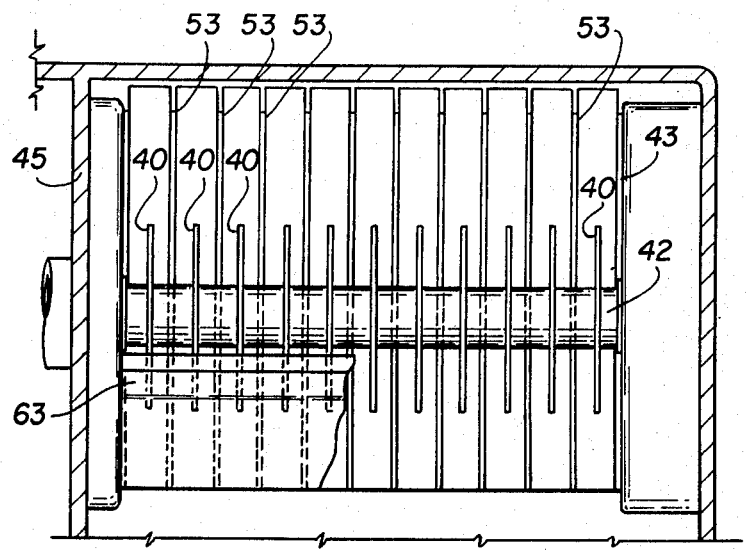
FIG. 6 is a view taken along the stepped line 6—6 in FIG. 5 showing the destruction apparatus in detail.
Figure 10:
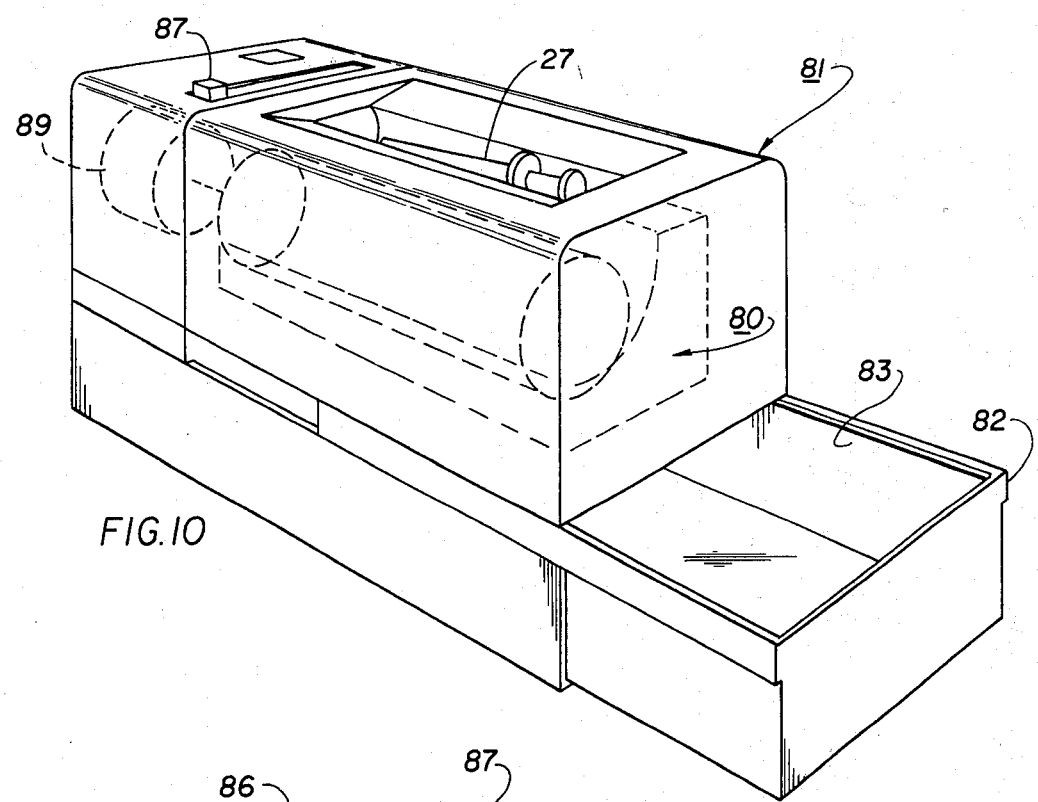
FIG. 10 is a perspective view of another embodiment of the present invention.
Figure 11:
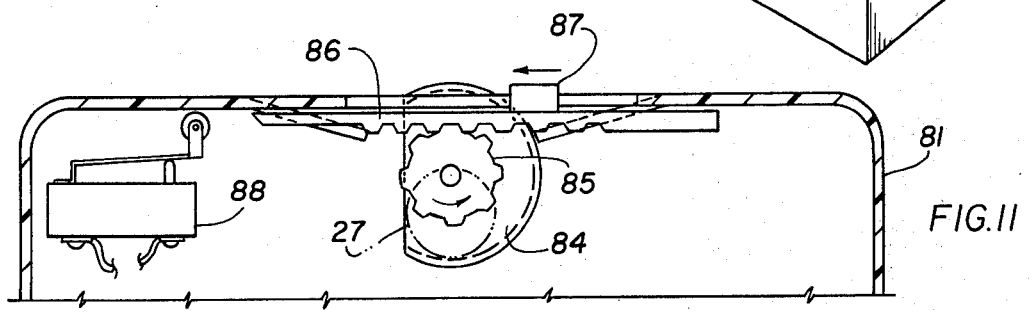
FIG. 11 is a partial sectional view of the syringe insertion mechanism and on-off switch.
Figure 12:
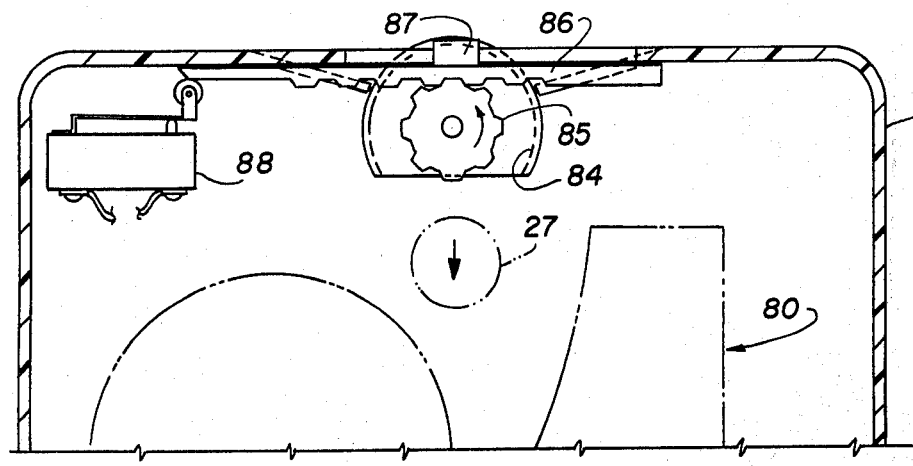

Referring to FIGS. 10-12, a further embodiment of the present invention is illustrated which utilizes a cutting mechanism 80 which is substantially identical with the cutting mechanism of FIG. 6. Due to a different type of housing for the apparatus, a different type of drive mechanism, using differently shaped gears and motor (not shown) are used.

Referring specifically to FIG. 10, the alternative arrangement comprises a housing 81 with a drawer 82 slideably arranged therein. Within the drawer is placed a disposable liner 83 comprised for example, of cardboard, or the like. In the upper section of the device is located the cutting mechanism 80, as indicated generally by the dashed lines in FIG. 10.

FIGS. 10-12 show the syringe insertion mechanism and on-off switch arrangement of this embodiment which constitute additional novel features. The syringe receptacle 84 is pivotally mounted to the housing 81 and has a gear 85 secured at one end thereof. At the end of the receptacle 84 that has the gear 85 thereon is slideably mounted a rack 86 which engages the gear 85. The rack 86 has an on-off lever 87 secured thereto. In FIG. 10, the apparatus is shown with the receptacle 84 in the position to accept a syringe 27 therein. In FIG. 11, the apparatus is shown with the receptacle 84 in the partially operated state, and FIG. 12 illustrates the apparatus with the receptacle in the fully closed state, the syringe 27 falling therefrom and into the destruction mechanism 80. When the receptacle is in the condition shown in FIG. 12, the bottom end thereof becomes upright, thus blocking the receptacle slot completely, thereby rendering the device safe during use.

As shown in FIG. 12, when the rack 86 is moved to its fully operative position the end thereof engages an on-off switch 88 which is operatively coupled to the motor which drives the destruction mechanism 80. This interlock further enhances the safety of the device during use.

Preferably, as with the previously described embodiment, the cutting mechanism 80 is completely removable and autoclavable, and the receptacle 82 is likewise completely removable and autoclavable. The motor drive for the destruction mechanism 80 is preferably located within the lefthand portion of the housing as seen in FIG. 10 and is shown generally by the dashed-line block 89.

As used hereinabove and in the appended claims, the terms "teeth" or "serrations" as used to describe the periphery of the wheels 40 and the portion A of fixed cutters 53 are used interchangeably. Only the term "serrations" is used in the appended claims for convenience of description.

While the invention has been described above with respect to specific embodiments, it should be clear that many modifications and alterations may be made thereto without departing from the inventive concept as set forth in the appended claims. For example, the structure may be modified so as to accommodate the invention to a particular use, and the invention may be used for destroying items other than the syringes which are presently and generally used in the medical field. Depending upon the materials of the items to be destroyed, various modifications and alterations to the destruction mechanism and/or the speed of operation thereof, are contemplated within the scope of the invention.

I claim:

1. A cartridge arrangement for containing a plurality of syringes, or like objects, for selective insertion of said syringes into a destruction mechanism of a destruction device, comprising:
   a cartridge body adapted to be movably mounted to said destruction device, and including means defining a plurality of chambers therein, each chamber retaining at least one syringe; and
   a slideable base member mounted to said cartridge body for selective sliding relative to said cartridge body for selectively opening said chambers to deposit syringes from the selectively opened chambers into said destruction mechanism, said slideable base member including means engageable with said destruction device for opening said chambers upon advancing movement of said cartridge body relative to said destruction device.

2. A cartridge arrangement according to claim 1 comprising means for engaging said destruction device for selectively feeding syringes from said chambers thereto.

3. A cartridge arrangement according to claim 2 wherein said engaging means comprises gear means for advancing said cartridge body relative to said destruction device, and detent means for positively locating said cartridge body relative to said destruction device.

4. A cartridge arrangement according to claim 1 comprising a handle means mounted to said cartridge body to facilitate handling thereof.

5. A cartridge arrangement according to claim 1 wherein said cartridge body includes an openable cover for selectively opening and closing said chambers for insertion of syringes therein.

6. A cartridge arrangement according to claim 5 comprising a handle means mounted to said cover to facilitate handling of said cartridge body.

7. A cartridge arrangement according to claim 2 wherein said gear means comprises an elongated rack gear on said cartridge body and adapted to engage a mating gear of said destruction device.

8. A cartridge arrangement according to claim 3 wherein said detent means include an elongated member with a plurality of detents therein, said elongated member being on said cartridge body and being adapted to engage a detent engaging means on said destruction device.

9. A cartridge arrangement according to claim 8 wherein said gear means comprises an elongated rack gear on said cartridge body and adapted to engage a mating gear of said destruction device.

10. A cartridge arrangement according to claim 3 wherein said detent means comprises means for positively locating said cartridge body in a plurality of predetermined positions relative to said destruction device.

* * * * *

UNITED STATES PATENT AND TRADEMARK OFFICE
CERTIFICATE OF CORRECTION

PATENT NO. : 3,995,768
DATED : December 7, 1976
INVENTOR(S) : Anthony P. MONTALBANO It is certified that error appears in the above-identified patent and that said Letters Patent are hereby corrected as shown below:

Title page, next to "[75]", change "Inventors" to --Inventor-- and delete "Erich Emil Hensel, Wassenaar, Netherlands"

Signed and Sealed this

Eighth Day of February 1977

[SEAL]

*Attest:*

RUTH C. MASON
*Attesting Officer*

C. MARSHALL DANN
*Commissioner of Patents and Trademarks*